(12) United States Patent
Ewer et al.

(10) Patent No.: US 10,206,343 B2
(45) Date of Patent: Feb. 19, 2019

(54) NUTRIENT DELIVERY SYSTEM

(71) Applicant: EwerSmith Enterprises, LLC, Forest Grove, OR (US)

(72) Inventors: Fred Lee Ewer, Forest Grove, OR (US); Christopher Harry Smith, Port Saint Lucie, FL (US); Alan Leroy Harris, Ogden, UT (US)

(73) Assignee: EwerSmith Enterprises, LLC, Forest Grove, OR (US)

( * ) Notice: Subject to any disclaimer, the term of this patent is extended or adjusted under 35 U.S.C. 154(b) by 388 days.

(21) Appl. No.: 14/924,580

(22) Filed: Oct. 27, 2015

(65) Prior Publication Data
US 2017/0112080 A1    Apr. 27, 2017

(51) Int. Cl.
*A01G 27/00* (2006.01)
*A01G 25/16* (2006.01)
*G01N 33/00* (2006.01)

(52) U.S. Cl.
CPC ......... *A01G 27/003* (2013.01); *A01G 25/165* (2013.01); *G01N 33/0098* (2013.01)

(58) Field of Classification Search
CPC .... A01G 27/00; A01G 27/003; A01G 27/001; A01G 27/008; A01G 25/165; A01G 25/16
See application file for complete search history.

(56) References Cited

U.S. PATENT DOCUMENTS

| | | | | |
|---|---|---|---|---|
| 3,758,987 A | * | 9/1973 | Crane, Jr. | A01G 27/003 137/78.3 |
| 4,083,147 A | * | 4/1978 | Garrick | A01G 27/003 137/397 |
| 4,653,529 A | * | 3/1987 | Freeman | A01G 27/001 137/453 |
| 4,685,827 A | * | 8/1987 | Sibbel | A01G 27/005 239/542 |
| 4,755,942 A | * | 7/1988 | Gardner | A01G 25/16 47/1.01 R |
| 4,834,265 A | * | 5/1989 | Snyder | A01G 27/003 222/1 |

(Continued)

FOREIGN PATENT DOCUMENTS

| | | | | |
|---|---|---|---|---|
| DE | 29709421 U1 | * | 7/1997 | A01G 27/003 |
| DE | 102016109747 A1 | * | 12/2016 | A01G 25/167 |

(Continued)

*Primary Examiner* — Magdalena Topolski
(74) *Attorney, Agent, or Firm* — Klarquist Sparkman, LLP

(57) ABSTRACT

A plant nutrient delivery system comprises a sensor, an electronically actuated valve and an electronic controller. The sensor is positionable in plant growing media and operable to detect a condition of the plant growing media. The electronically actuated valve has a connection to a liquid nutrient source. The electronic controller is linked to the sensor and to the electronically actuated valve. The controller is programmed to carry out automatic demand-based nutrient delivery to the plant growing media by controlling the electronically actuated valve to turn on and off based on signals received from the sensor regarding a condition of the plant growing media, thereby causing a flow of the liquid nutrient into the plant growth media to start and to stop. Methods are also described.

14 Claims, 16 Drawing Sheets

(56) References Cited

U.S. PATENT DOCUMENTS

| | | | | |
|---|---|---|---|---|
| 4,846,206 | A * | 7/1989 | Peterson | A01G 27/001 137/1 |
| 4,934,096 | A * | 6/1990 | Bentvelsen | A01G 27/003 47/62 N |
| 5,046,282 | A * | 9/1991 | Whitaker | A01G 27/003 47/79 |
| 5,279,071 | A * | 1/1994 | McDougall | A01G 27/003 428/16 |
| 5,315,787 | A * | 5/1994 | Schleicher | A01G 27/003 222/66 |
| 5,511,341 | A * | 4/1996 | Payne | A01G 27/003 239/302 |
| 5,601,236 | A * | 2/1997 | Wold | A01G 27/00 239/63 |
| 5,634,342 | A * | 6/1997 | Peeters | A01G 27/003 47/79 |
| 5,921,025 | A | 7/1999 | Smith | |
| 6,622,430 | B1 * | 9/2003 | Lai | A01G 27/005 47/79 |
| 7,059,367 | B2 * | 6/2006 | Atkinson | A01G 27/02 137/393 |
| 7,349,764 | B2 * | 3/2008 | Haupt | A01G 25/167 137/78.2 |
| 7,703,240 | B2 * | 4/2010 | Watson | A01G 27/06 47/65.5 |
| 8,793,024 | B1 * | 7/2014 | Woytowitz | A01G 25/167 137/78.2 |
| 9,661,810 | B2 * | 5/2017 | Walker, II | A01G 27/02 |
| 9,807,949 | B2 * | 11/2017 | Hamlin | A01G 31/02 |
| 2003/0000573 | A1 * | 1/2003 | Yoshioka | A01G 27/003 137/78.3 |
| 2004/0195372 | A1 * | 10/2004 | Yoshikawa | A01G 25/165 239/310 |
| 2006/0217845 | A1 * | 9/2006 | Simon | A01G 25/165 700/284 |
| 2007/0057801 | A1 | 3/2007 | Hawker | |
| 2008/0078786 | A1 * | 4/2008 | Aazami | A01G 25/165 222/644 |
| 2008/0190020 | A1 * | 8/2008 | Todd | A01G 25/167 47/48.5 |
| 2008/0302002 | A1 * | 12/2008 | Schmidt | A01G 25/167 47/48.5 |
| 2010/0230510 | A1 * | 9/2010 | Wilson | A01G 25/16 239/70 |
| 2010/0307057 | A1 * | 12/2010 | Hashimoto | A01G 25/06 47/79 |
| 2011/0017845 | A1 * | 1/2011 | Crist | A01G 25/16 239/569 |
| 2012/0083929 | A1 * | 4/2012 | Conrad, Jr. | A01G 9/02 700/284 |
| 2013/0079934 | A1 * | 3/2013 | Carskadon | A01G 27/001 700/282 |
| 2013/0255783 | A1 * | 10/2013 | Runge | A01G 25/167 137/1 |
| 2014/0007501 | A1 * | 1/2014 | Griebel | H04B 7/022 47/48.5 |
| 2015/0136241 | A1 * | 5/2015 | Nguyen | A01G 27/005 137/130 |
| 2015/0173301 | A1 * | 6/2015 | Mahan | A01G 27/003 47/58.1 FV |
| 2015/0223416 | A1 * | 8/2015 | Eng | A01G 25/167 700/284 |
| 2015/0230417 | A1 * | 8/2015 | Nickerson | A01G 25/16 700/284 |
| 2015/0264859 | A1 * | 9/2015 | Morrissey | A01G 9/02 700/282 |
| 2015/0289463 | A1 * | 10/2015 | Moriarty | A01G 31/02 47/62 R |
| 2015/0327449 | A1 * | 11/2015 | Bartlett | A01G 25/167 137/15.08 |
| 2016/0174477 | A1 * | 6/2016 | Li | A01G 27/003 47/48.5 |
| 2016/0183483 | A1 * | 6/2016 | Sharif | A01G 25/165 700/284 |
| 2016/0219806 | A1 * | 8/2016 | Thiessen | A01G 25/165 |
| 2016/0345517 | A1 * | 12/2016 | Cohen | A01G 31/02 |
| 2016/0366843 | A1 * | 12/2016 | Evans | A01G 27/003 |
| 2017/0000048 | A1 * | 1/2017 | Ference | A01G 27/003 |
| 2017/0042101 | A1 * | 2/2017 | Soltani | A01G 27/003 |
| 2017/0215355 | A1 * | 8/2017 | Johnson | A01G 27/003 |
| 2017/0238484 | A1 * | 8/2017 | Arumugam | A01G 25/16 |
| 2017/0286772 | A1 * | 10/2017 | Workman | G06K 9/00657 |
| 2017/0326572 | A1 * | 11/2017 | Goerdt | B05B 15/10 |
| 2017/0339841 | A1 * | 11/2017 | Monasterio | A01G 9/02 |

FOREIGN PATENT DOCUMENTS

| | | | | |
|---|---|---|---|---|
| EP | | 2294911 A2 * | 3/2011 | A01G 27/003 |
| EP | | 2540155 A1 * | 1/2013 | A01G 27/02 |
| EP | | 3033940 A1 * | 6/2016 | A01G 27/008 |
| FR | | 2657496 A1 * | 8/1991 | A01G 27/003 |
| FR | | 2666719 A1 * | 3/1992 | A01G 27/003 |
| WO | WO-8905576 A1 * | | 6/1989 | A01G 27/003 |
| WO | WO-2011155677 A1 * | | 12/2011 | A01G 27/003 |

* cited by examiner

NUTRIENT DELIVERY SYSTEM

BACKGROUND

The present application relates to plants and plant nutrients, and in particular to a nutrient delivery system that automatically delivers nutrients (including water and other nutrients) to plants according to sensed conditions in the plant's environment.

Automatic watering devices for plants typically incorporate an electrically actuated valve and a timer. According to this approach, water is delivered to the plants based on preset times of day and durations. Users typically guess at an appropriate time(s) of day and duration(s), which likely results in over watering or under watering the plants. A plant's need for water and other nutrients changes with weather conditions (including temperature and precipitation), sunlight, evaporation rate, soil conditions and the plant's size, among other factors. As a result, it is very difficult to deliver the appropriate amount of water for the plant at the current time with the typical approaches.

In addition, the typical approaches cause waste because of over watering and loss of plants and/or plant yield due to under watering in some conditions.

DETAILED DESCRIPTION

Figure 1:
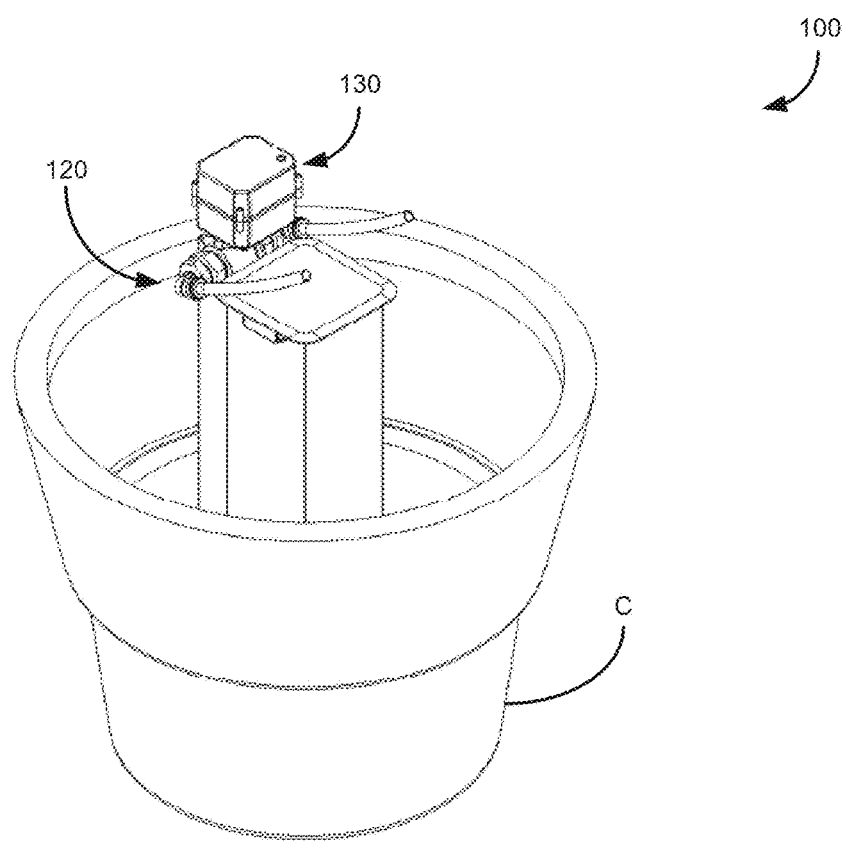
FIG. 1 is a perspective view of a nutrient delivery system installed in a conventional container, such as a conventional pot.
Figure 2:
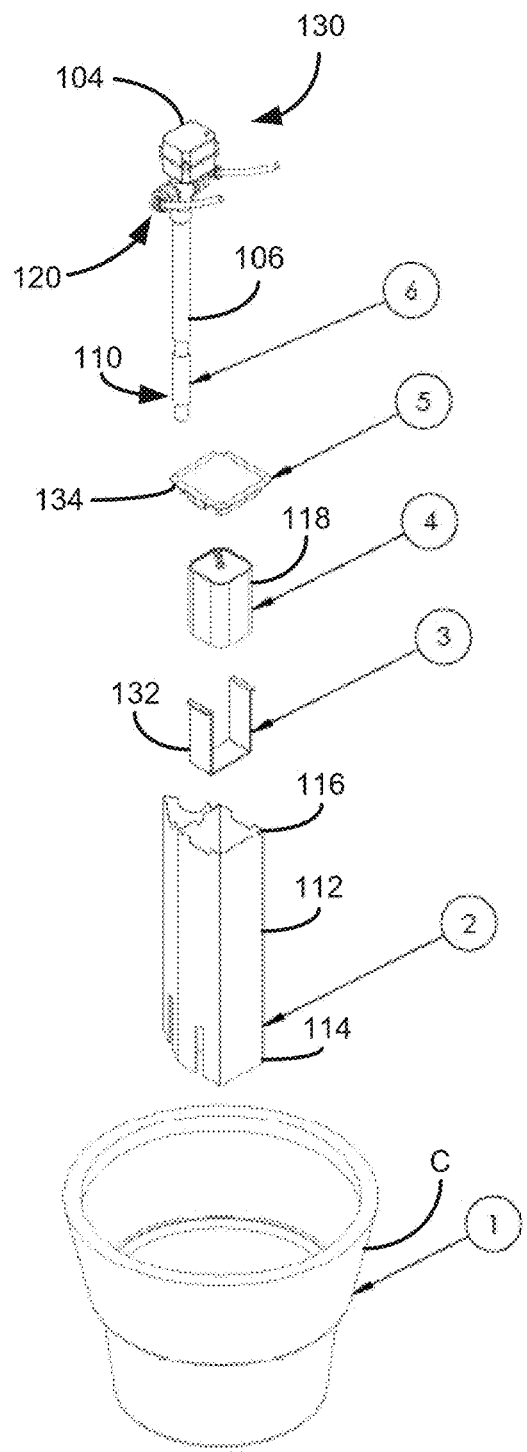
FIG. 2 is an exploded perspective view of the nutrient delivery system of FIG. 1.

According to representative implementations, and as shown in FIGS. 1 and 2, a nutrient delivery system 100 has a sensor 110, a valve 120 and a controller 130 that is linked to the sensor 110 and to the valve 120. As explained in more detail below, the controller 130 is programmed to automatically operate the valve 120 according to predetermined conditions. As shown, the nutrient delivery system 100 according to some implementations is configured for use in conjunction with a container C within which one or more plants can be grown, but other configurations are also possible.

The nutrient delivery system 100 can have a housing 104 coupled to the valve 120 and a riser 106 connected to one of the valve's fluid passages. The housing 104 can be sized to at least partially enclose and protect the controller 130 and other circuit elements (discussed below in greater detail) from moisture and other environmental conditions. In the illustrated implementation, the sensor 110 is connected to the controller 130 by a sensor wire (not shown). In other implementations, the sensor 110 and the controller can communicate wirelessly. Power can be supplied to the circuit by a battery 118.

The nutrient delivery system can have a support 112. In the illustrated implementation, the support is sized to support the valve 120 and housing 104, such as at a position above a level of plant growing media P (FIG. 3) in the container C. At its upper end 116, the support 112 defines a space or recess sized to receive the battery 118 and has a longitudinal bore sized to receive the riser 106. A lower end 114 of the support is designed to be positioned in or pushed into the plant growing media P or other material in the container. As shown, the battery 118 can be received in a battery holder 132 positioned in the recess and the recess can be covered by a cap 134.

Figure 5:
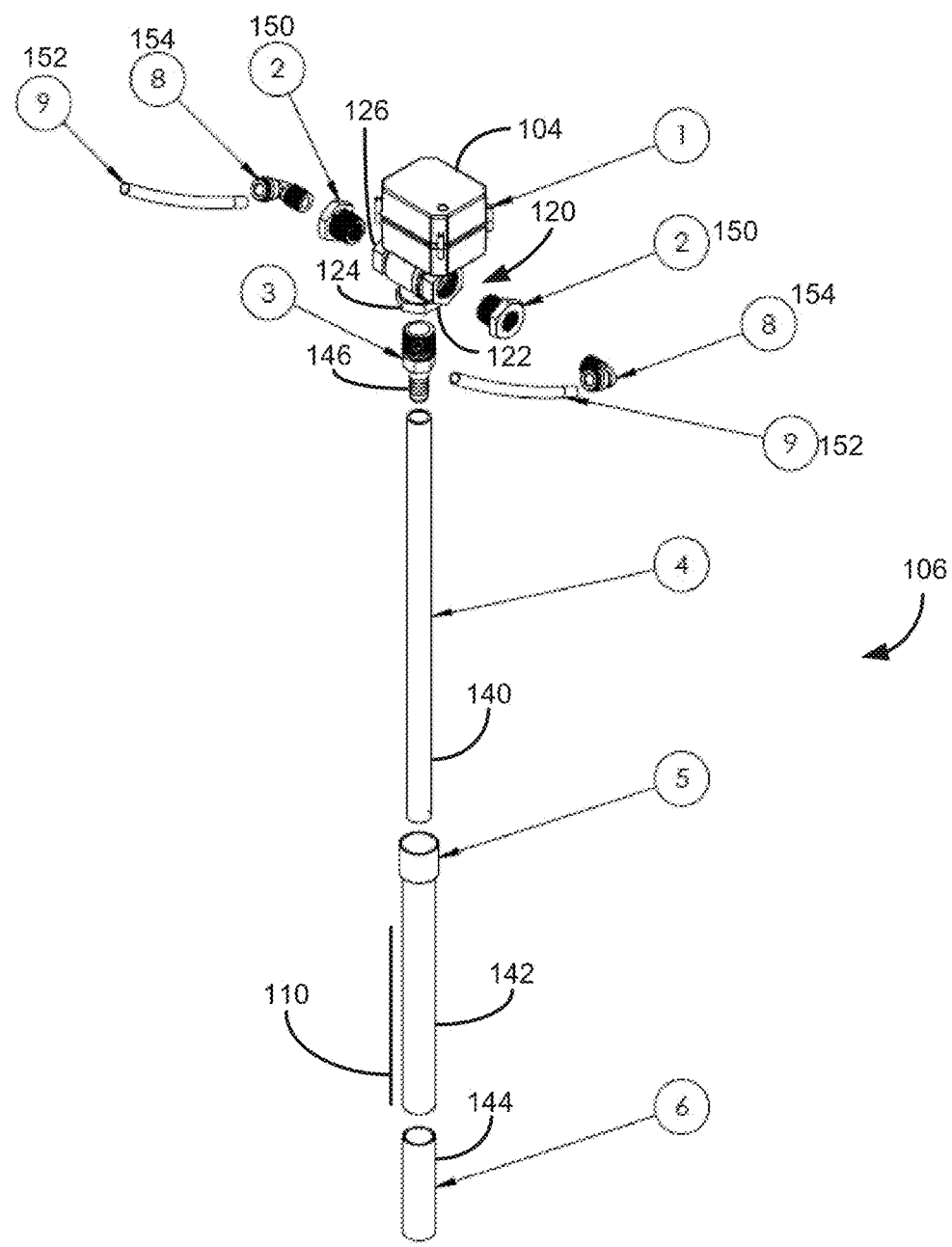
FIG. 5 is an exploded perspective view of a valve, riser, battery, reservoir assembly and other components of the nutrient delivery system
Figure 6:
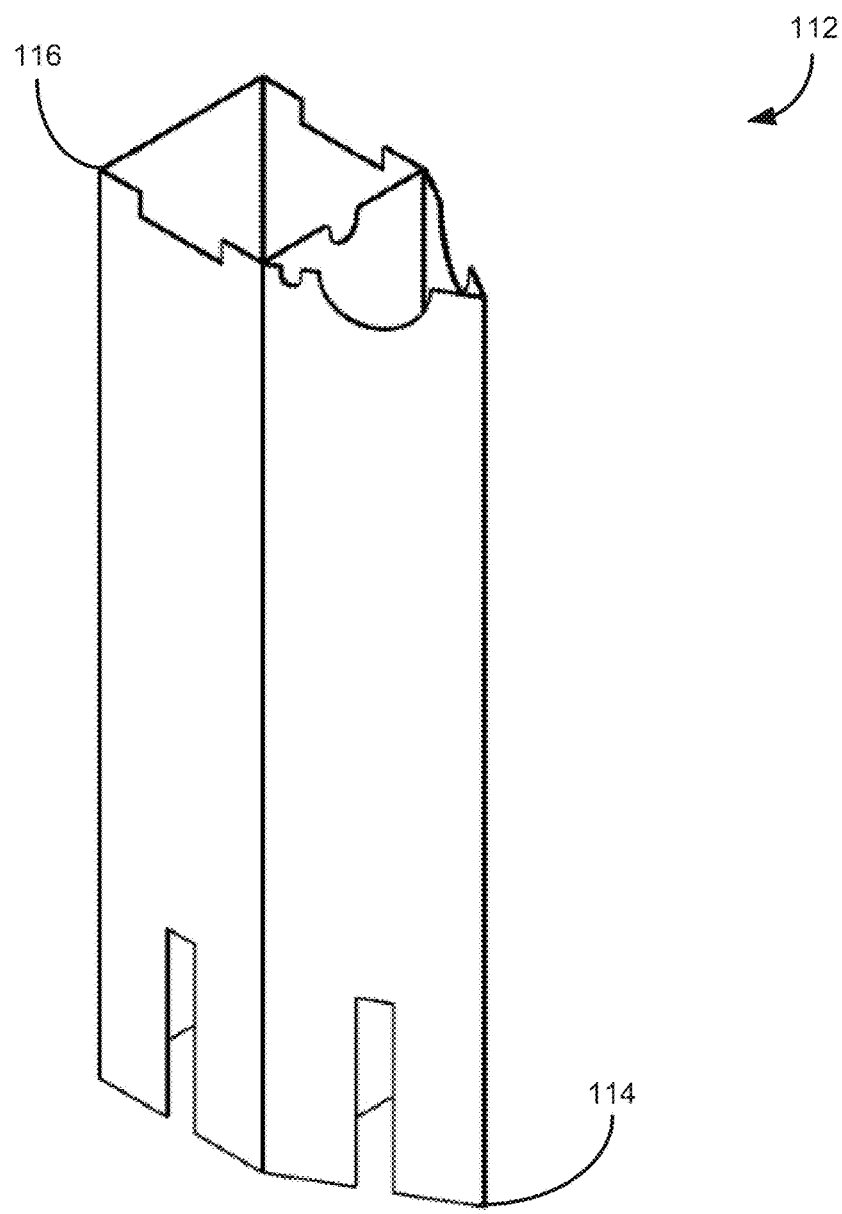
FIG. 6 is an enlarged perspective view of a reservoir assembly.

An implementation of the riser 106 and the valve 120 is shown in more detail in FIG. 5. As illustrated, the valve 120 provides for three connections, although other configurations are of course possible. There is a first inlet connection 122, which can be connected to a source of a liquid nutrient, such as water or water mixed with other ingredients (e.g., one or more fertilizing ingredients). In some implementations, the first inlet connection 122 is adapted for connection to a household hose bib (not shown) or other source of pressurized water. There is a first outlet connection 124 that is connected to the riser 106 and supplies flow to the container C under predetermined conditions. There is an optional second outlet connection 126, which, e.g., allows multiple instances of the nutrient delivery system 100 to be daisy chained together.

The riser 106 can have any suitable configuration, such as a length suitable to position the valve 120 and housing 104 above an upper end of the container C as shown.

The riser 106 can be assembled together from several segments. In the implementation shown in FIG. 5, the riser 106 has a single full length tube section 140 to which the sensor 110 is coupled. Optionally, there is a second larger diameter tube 142 for positioning along the upper length of the tube section 140. A length of heat shrink tubing 144 is used to secure the sensor 110 in place along the riser tube section 140 with its lower (low level sensing) end exposed and its upper (high level sensing) end exposed. The tube section 140 can be connected at its upper end to a suitable fitting 146.

Similarly, the first inlet connection 122 and the second outlet connection 126 can be configured to receive a suitable fitting 150, such as to allow connection to conventional ¼" drip irrigation tubing 152 and an elbow 154.

Figure 8:
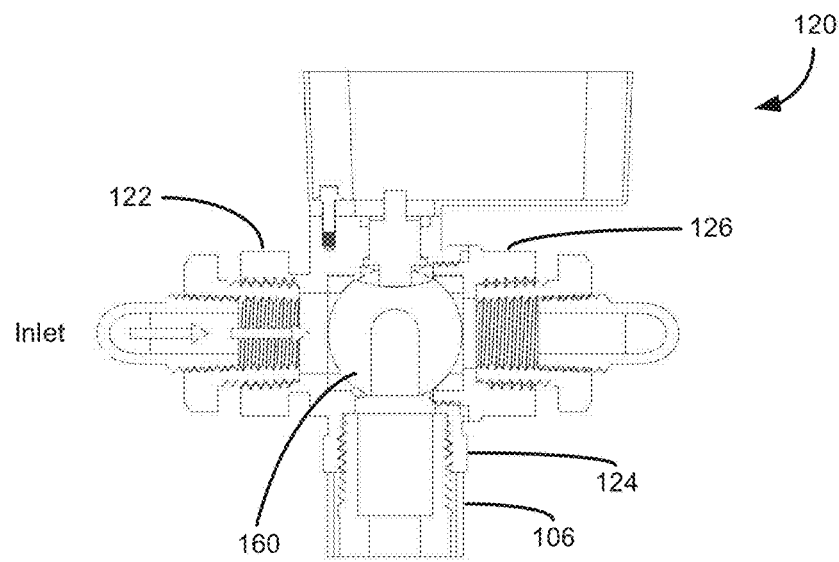
FIGS. 8 and 9 are sectioned plan views of the valve in two different operating positions.
Figure 9:
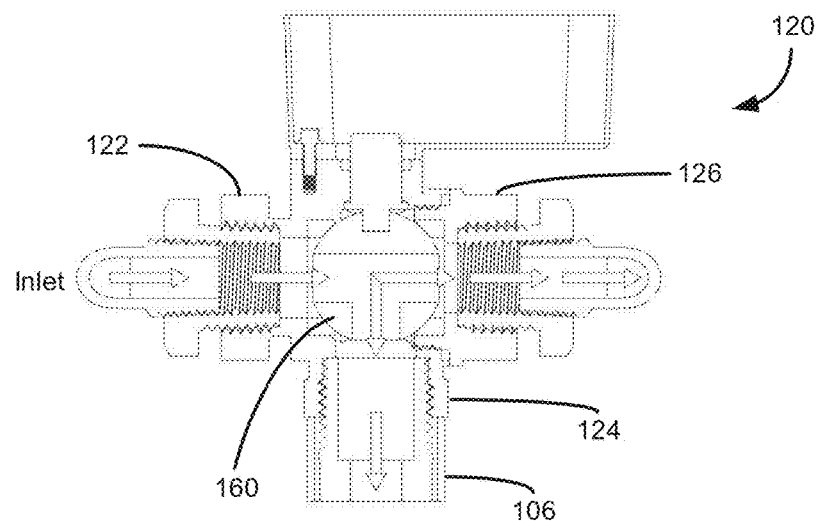

Referring to FIGS. 8 and 9, a representative construction of the valve 120 is shown in section. One suitable valve is the CWX-15 Series 3-way motorized valve having a brass construction and a customized controller. In FIG. 8, a ball element 160 has been moved to a closed position to stop flow from the inlet connection 122. In FIG. 9, the ball element 160 has been moved to an opened position to allow flow from the inlet connection 122, through the valve body and out through the outlet connection 124 and into the riser 106, and out through the second outlet connection 126. It is also possible to configure the valve 120 to have an opened position in which flow is allowed through only one of the outlet connection 124 and the outlet connection 126.

Figure 7:
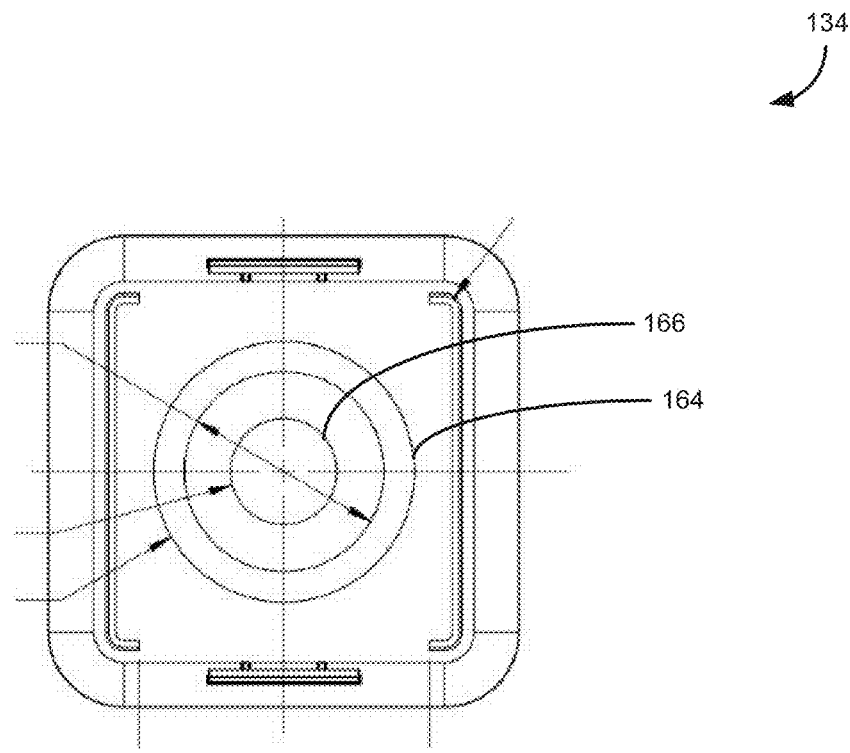
FIG. 7 is a plan view of an interior side of a cap.

FIG. 7 is a plan view showing an interior side of the cap 134. The cap be configured with conductive areas 164, 166 to connect with the battery 118. In some implementations, the battery 118 is a conventional 6V lantern cell.

Figure 10A:
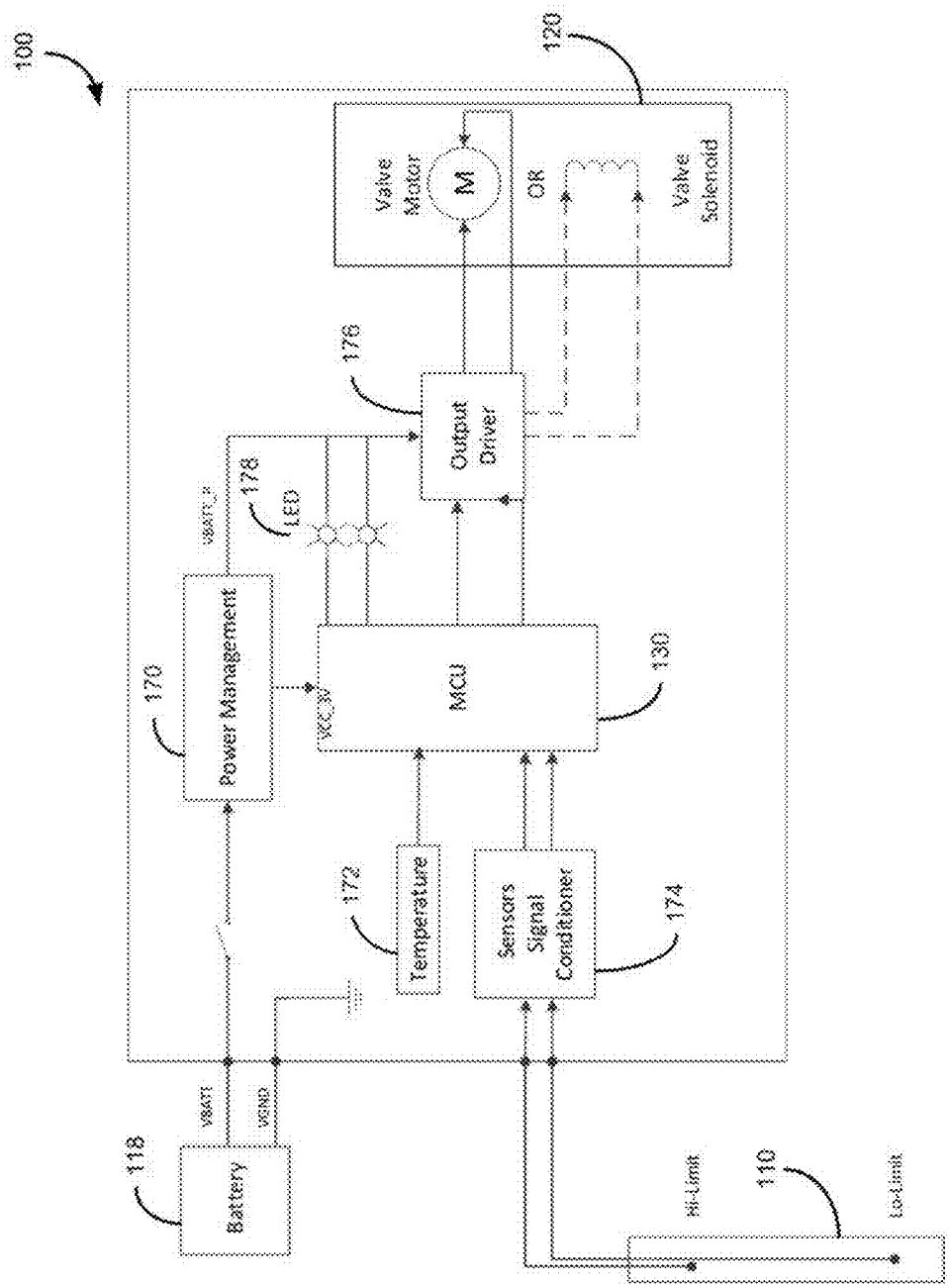
FIG. 10A is a block diagram of a representative nutrient delivery system.

FIG. 10A is a schematic block diagram of the nutrient delivery system 100. As shown, the controller (or MCU) 130 controls an output driver component 176 to send drive signals to move the valve 120, such as via a valve solenoid or a valve motor. The sensor 110 can be configured as a sensor probe 110 as shown, with a low level sensing portion or low level detector 111 and a high level sensing portion or high level detector 113 (see FIGS. 13A and 13B). The sensor signals can be received by a sensor signals conditioner 174, processed and sent to the controller 130. In addition to a liquid level or moisture sensor, there can be a temperature sensor 172 that detects an ambient temperature and sends a temperature signal to the controller 130. The battery 118 can be connected via a power management component 170 to supply appropriate power to the controller 130 and other components. One or more LEDs 178 or other similar indicators can be provided to signal conditions, such as sufficient battery level, low battery level, valve in operation, liquid or moisture level, etc.

Figure 3:
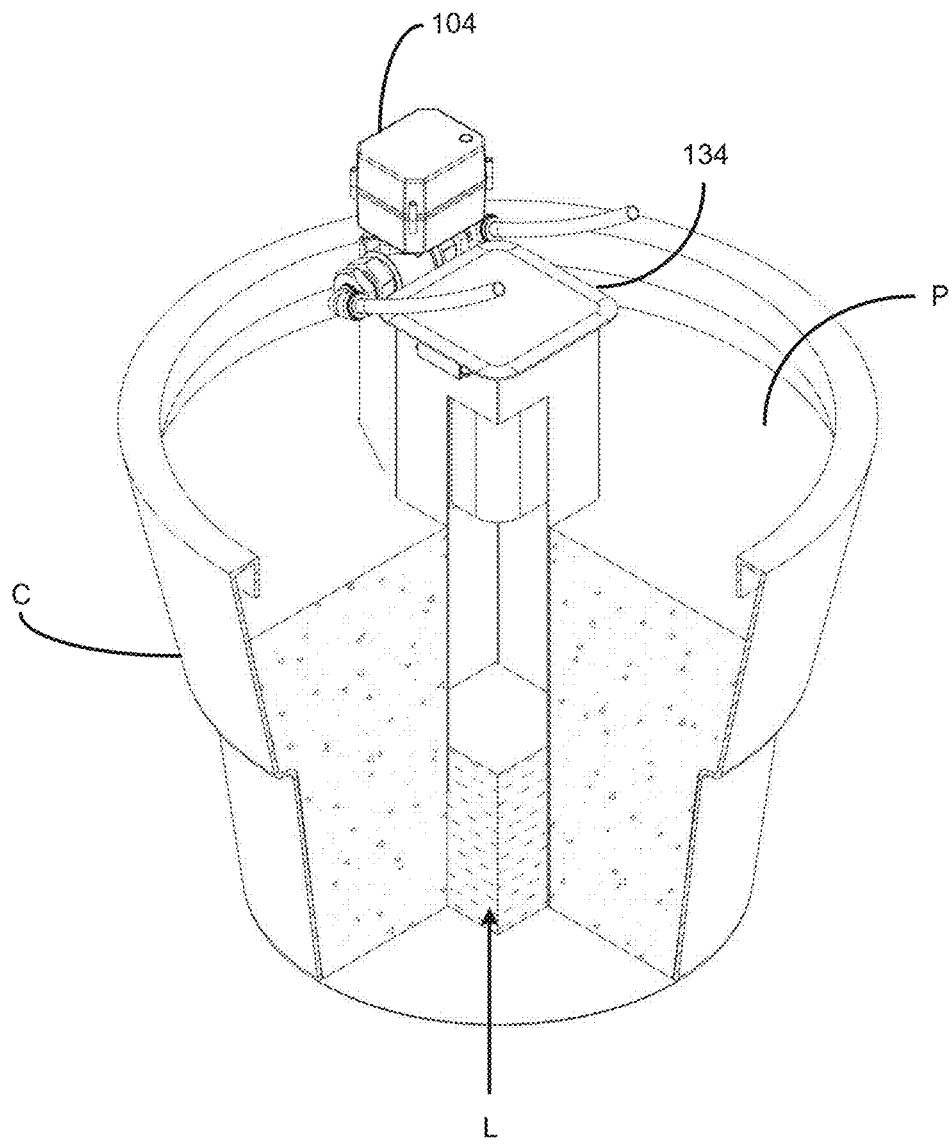
FIG. 3 is a perspective view similar to FIG. 1 that has been sectioned to show levels of a liquid nutrient and plant growing media in the container.
Figure 4:
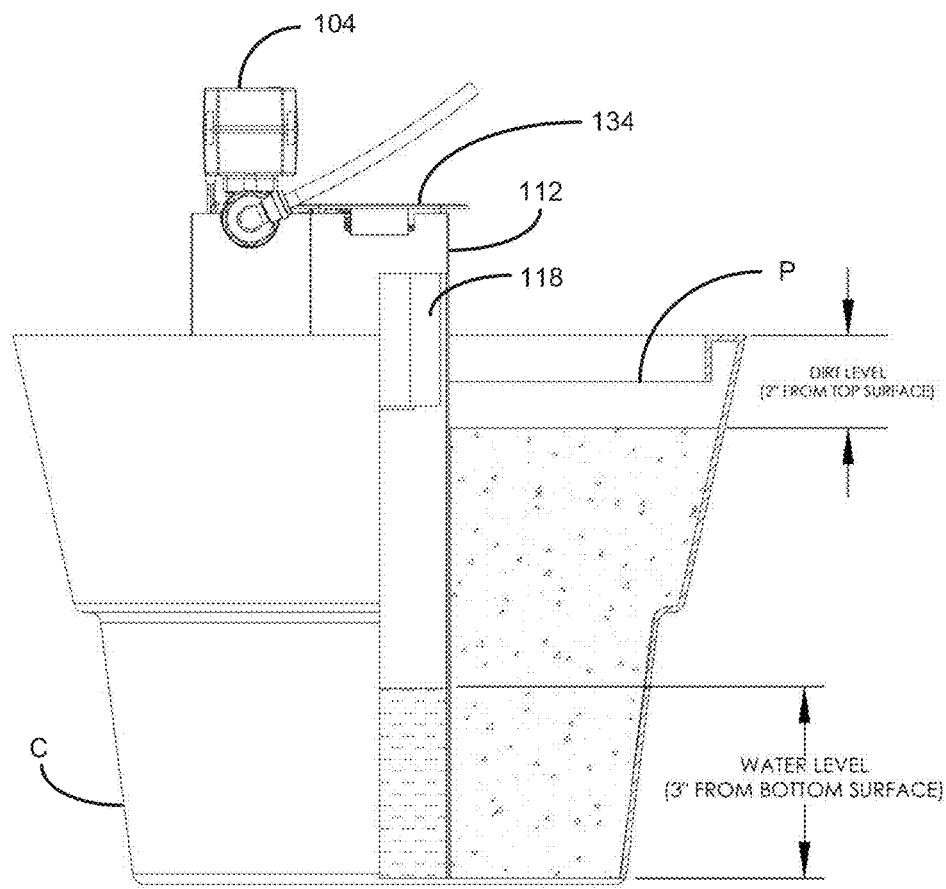
FIG. 4 is a sectioned side elevation view of the nutrient delivery system.

As shown in FIGS. 3 and 4, the nutrient delivery system can be configured to deliver liquid nutrient to the container C, on an on-demand basis, when a low level condition is sensed. In some implementations, the system is programmed to include an intentional delay, also called a stress cycle, in supplying the nutrient flow following a sensed low limit condition, because plant health increases if plants are appropriately stressed. Further, the stress cycle duration can be adjusted according to the ambient temperature such that only short stress cycles are used when ambient temperatures are high.

Figure 10B:
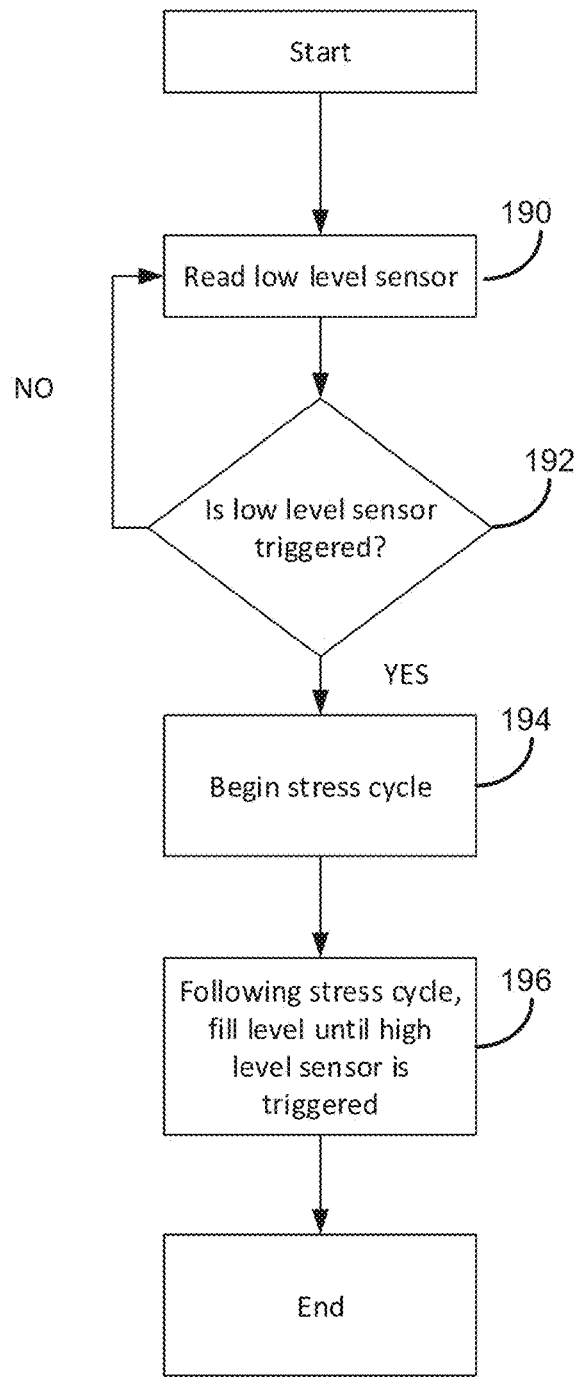
FIG. 10B is a flow chart of a representative method.

FIG. 10B is a flow chart showing steps of a representative method for operating the nutrient delivery system. According to step 190, the system reads the low level sensor. The interval between readings can be set to manage how much power the sensor drains from the battery. In one implementation, the low level sensor is read every 15 minutes. In step 192, the system determines if the low level sensor has been triggered, i.e., whether a level of moisture or liquid has fallen below a low limit as determined by the position of the low level sensor. If not, then the program returns to step 190 and reads the low level sensor at the next interval.

If the low level sensor has been triggered (see FIGS. 13A and 13B), then the system initiates a stress cycle (step 194). The stress cycle has a predetermined duration, and may be further modified according to ambient temperature, such as may be sensed by the temperature sensor 172. In one implementation, the stress cycle is set to 60 minutes. In step 196, following the completion of the stress cycle, the system turns the valve on to allow flow to fill the container until the high level is reached and the high level sensor is triggered.

Figure 13A:
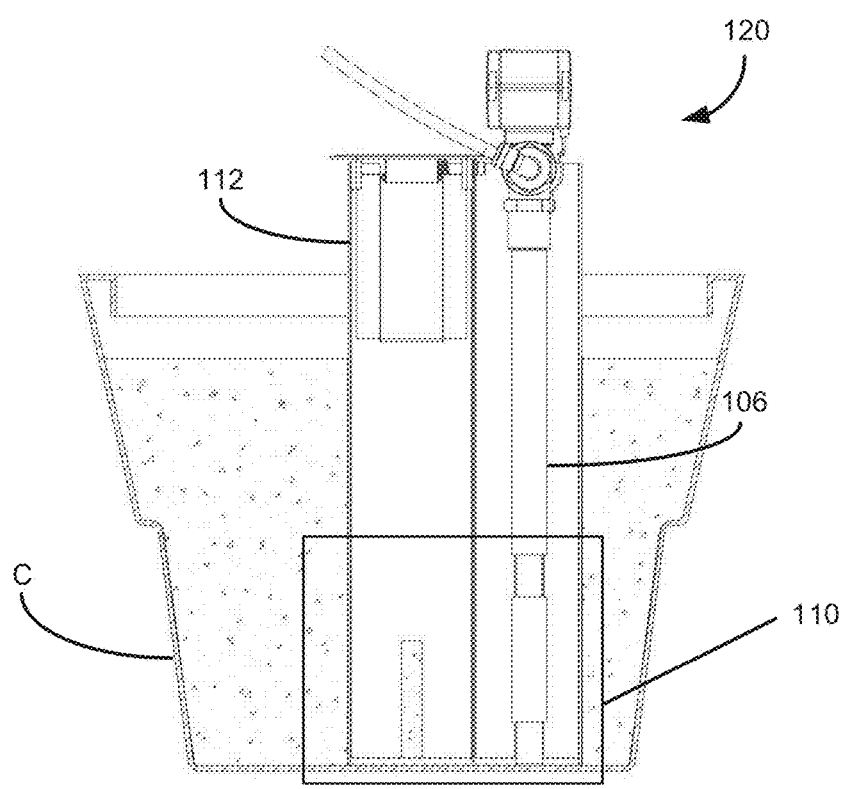
FIGS. 13A and 13B are sectioned side elevation views showing the system at a low level condition.
Figure 13B:
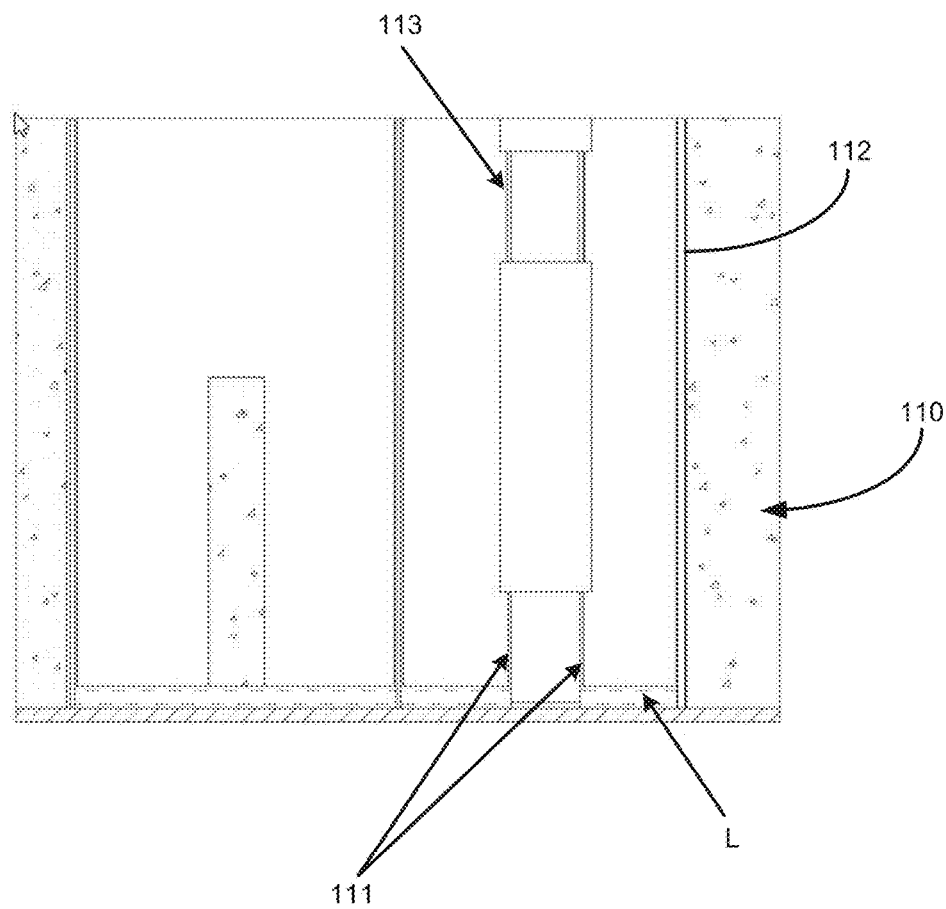
Figure 14A:
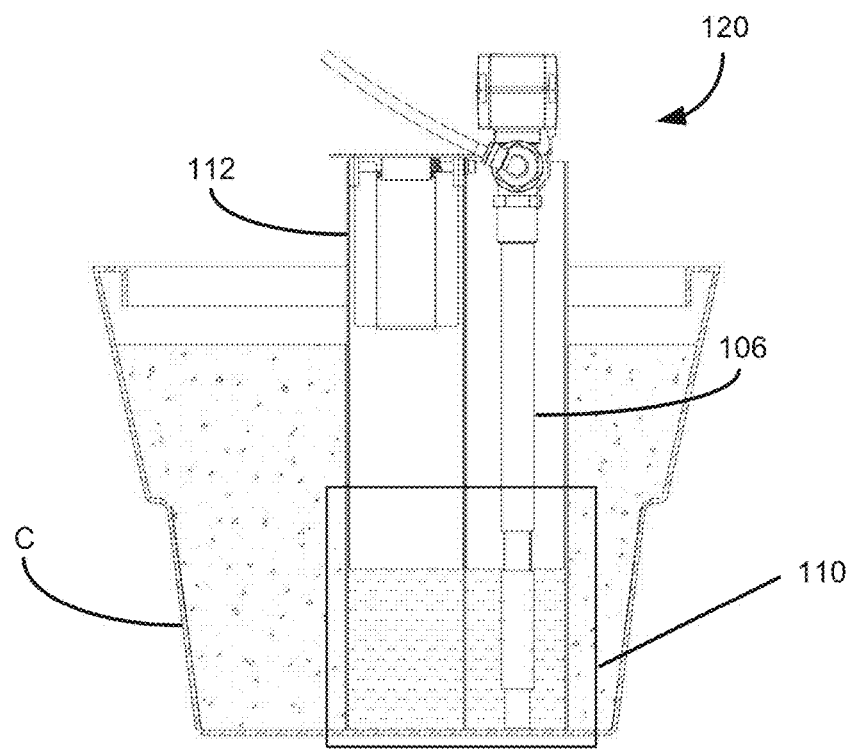
FIGS. 14A and 14B are sectioned side elevation views showing the system at a high level condition.
Figure 14B:
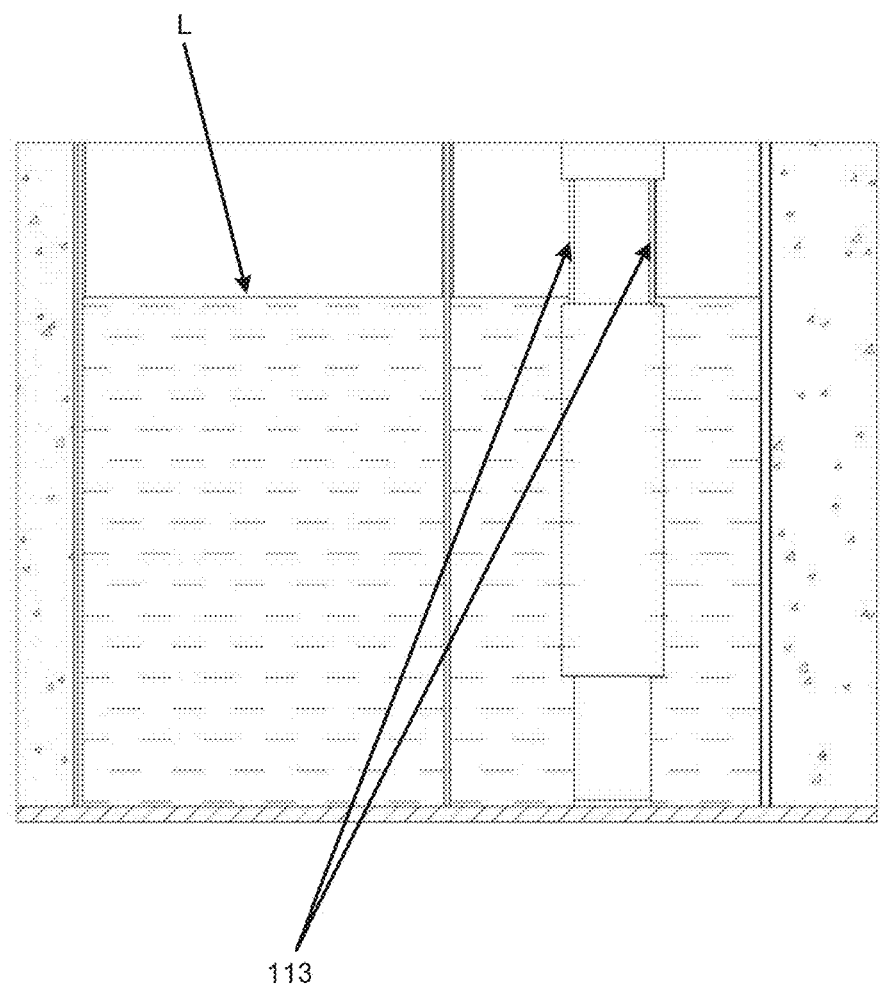

FIG. 13A shows a section view in elevation of the container C with the system 100 in a low level condition when the low level sensor 111 is being triggered. As shown in the magnified view of FIG. 13B, the water (or other liquid) at level L is contacting the low level detector 111. FIGS. 14A and 14B correspond to FIGS. 13A and 13B, respectively, but show the system after the stress cycle has been completed, after filling and upon the high level detector 113 detecting that the high level has been reached.

Figure 11:
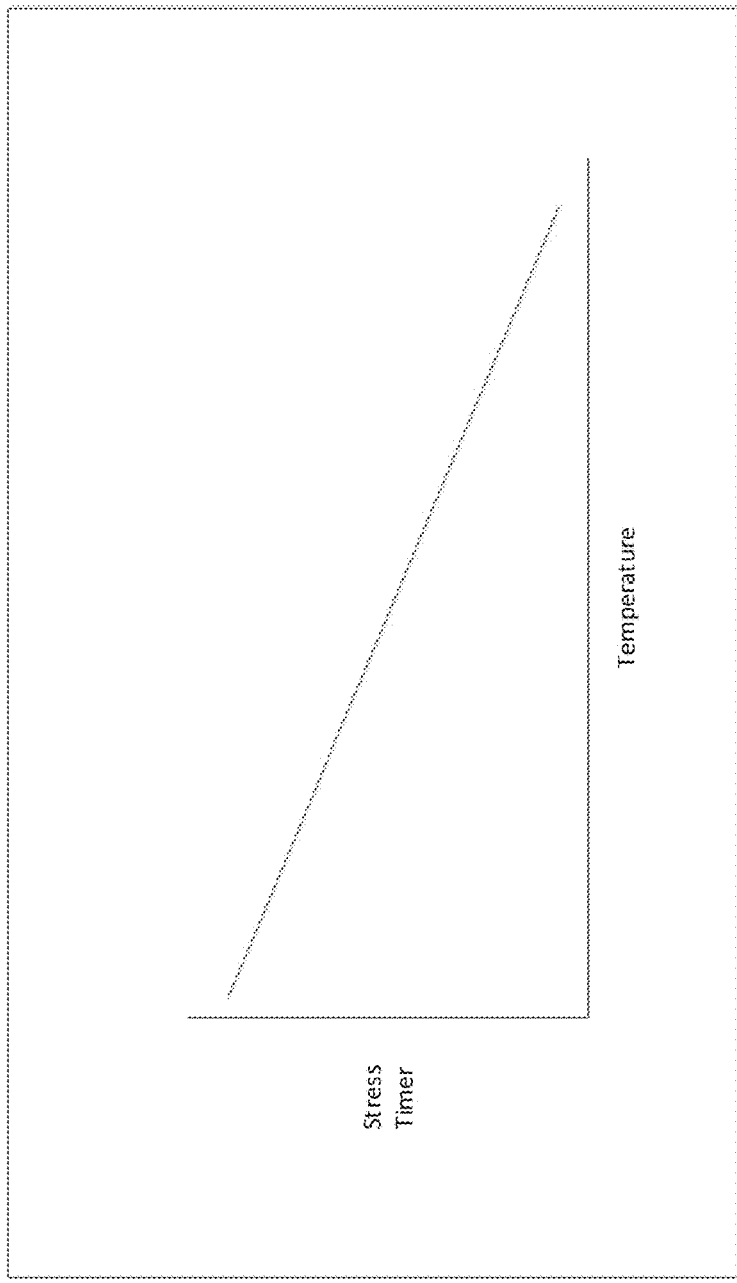
FIG. 11 is a graph of plant stress timer duration versus temperature.

FIG. 11 is a graph of temperature vs. a stress timer duration, showing that the duration of the stress period is decreased as the ambient temperature increases.

Figure 12:
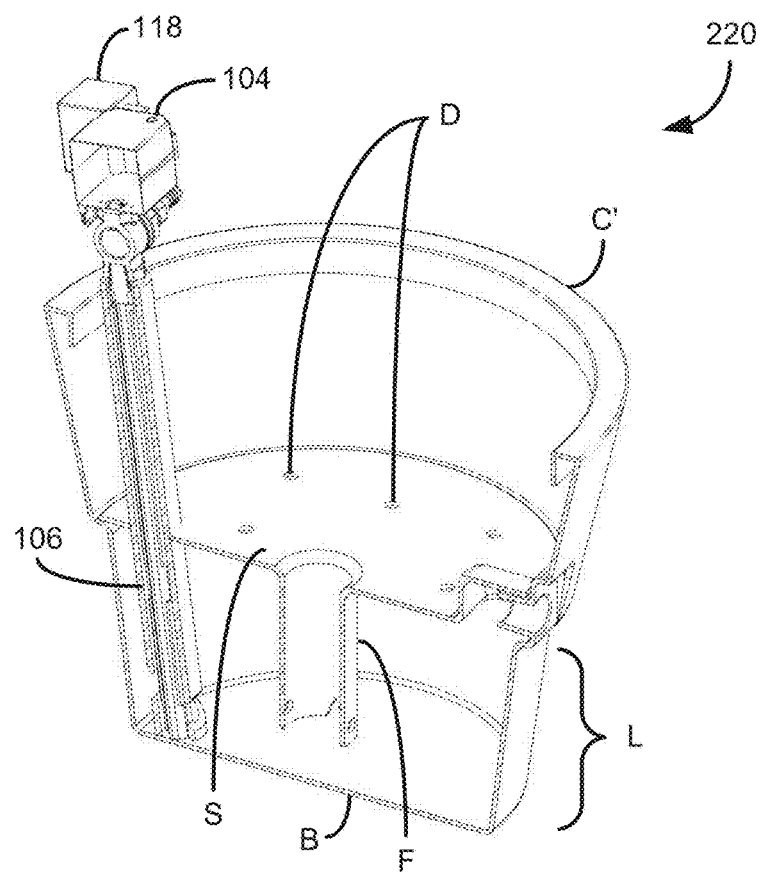
FIG. 12 is a sectioned perspective view showing a nutrient delivery system according to another implementation.

FIG. 12 is a sectioned perspective of a nutrient delivery system 200 according to another embodiment in which a container C' has an intermediate supporting surface S above a bottom B, and a lower chamber L is defined between the bottom and the supporting surface S. The intermediate supporting surface S supports plant support materials, such as plant growing media and other materials, above the bottom B. In this way, the lower chamber L serves as the reservoir, the riser 106 is used without a support 112, and a plant in the container draws liquid from the reservoir up through a central bore F by capillary action. Excess liquid can be returned to the lower chamber L via the drain holes D.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A plant nutrient delivery system, comprising:
a sensor and a riser, the sensor being coupled directly to the distal end of the riser, positionable in plant nutrient liquid in a plant nutrient liquid space and operable to sense a low level of the plant nutrient liquid indicating a condition of plant growth media located above and covering the plant nutrient liquid space;
an electronically actuated valve with a connection to a source of the plant nutrient liquid, the electronically actuated valve being coupled to the riser and spaced apart from the sensor, wherein the electronically actuated valve and riser are positionable in an operating position with the riser extending downwardly from the electronically-actuated valve and the sensor in the plant nutrient liquid space; and
an electronic controller linked to the sensor and to the electronically actuated valve, the controller being programmed to carry out automatic demand-based nutrient delivery by controlling the electronically actuated valve to turn on and off based on signals received from the sensor regarding the level of the plant nutrient liquid, thereby causing a flow of the plant nutrient liquid into the plant nutrient liquid space to start and to stop, wherein in response to the sensed low level, the controller initiates a stress cycle for a predetermined duration.

2. The plant nutrient delivery system of claim 1, wherein the plant nutrient liquid comprises water, and wherein the electronically actuated valve comprises a motorized valve connected to a source of household water.

3. The plant nutrient system of claim 1, further comprising a temperature sensor linked to the controller, and wherein the duration of the stress cycle is temperature dependent.

4. The plant nutrient system of claim 1, wherein the sensor comprises a low level detector for detecting the low level, further comprising a high level detector for detecting a high level of the plant nutrient liquid.

5. The plant nutrient system of claim 4, wherein the controller is programmed to send instructions to close the valve upon receiving a signal from the high level detector indicating that a predetermined high level has been reached.

6. The plant nutrient system of claim 1, wherein the controller is programmed upon completion of the stress cycle to send instructions to the valve to open and to supply plant nutrient liquid to the plant nutrient liquid space.

7. The plant nutrient system of claim 1, wherein the controller is programmed to send instructions to the valve to close when the controller receives a predetermined signal indicating the condition of the plant growth media.

8. A demand-based automatic plant nutrient delivery system, comprising:
- a sensor positionable in plant nutrient liquid in a plant nutrient liquid space and operable to sense a low level of the plant nutrient liquid indicating a condition of plant growth media located at a level above the plant nutrient liquid space;
- an electronically actuated valve, the valve comprising an inlet connection connectible to a source of the plant nutrient liquid, a first outlet connection connected to a riser and a second outlet connection for distributing flow from the first inlet connection to a downstream use, wherein the riser is positionable to extend into the plant nutrient liquid space and has a distal end to which the sensor is directly coupled; and
- an electronic controller linked to the sensor and to the electronically actuated valve, the controller being programmed to carry out demand-based nutrient delivery by controlling the valve to turn on and off based on signals received from the sensor regarding the level of plant nutrient liquid, thereby causing a flow of the plant nutrient liquid into the plant nutrient liquid space to start and to stop, wherein in response to the sensed low level, the controller initiates a stress cycle for a predetermined duration.

9. The plant delivery system of claim 8, wherein the plant nutrient liquid comprises water, the plant nutrient liquid in the plant nutrient liquid space being transportable to the level of the plant growth media by capillary action, and wherein the electronically actuated valve comprises a motorized valve connected to a source of household water.

10. The plant nutrient system of claim 8, further comprising a temperature sensor linked to the controller, and wherein the duration of the stress cycle is temperature dependent.

11. The plant nutrient system of claim 8, wherein the sensor comprises a high level detector for detecting a high level of plant nutrient liquid.

12. The plant nutrient system of claim 8, wherein the controller is programmed upon completion of the stress cycle to send instructions to the valve to open and to supply plant nutrient liquid to the plant nutrient liquid space.

13. The plant nutrient system of claim 12, wherein the controller is programmed to send instructions to close the valve upon receiving a signal from the high level detector indicating that a predetermined high level of plant nutrient liquid has been reached.

14. The plant nutrient system of claim 8, wherein the controller is programmed to read the sensor at a predetermined interval to determine if the low level has been reached.

* * * * *